US010031025B2

(12) United States Patent
Berghaus

(10) Patent No.: US 10,031,025 B2
(45) Date of Patent: Jul. 24, 2018

(54) COLOUR STRENGTH MEASUREMENT AND ITS USE IN PRODUCTION PROCESSES

(71) Applicant: COLVISTEC AG, Berlin (DE)

(72) Inventor: Andreas Werner Berghaus, Berlin (DE)

(73) Assignee: COLVISTEC AG, Berlin (DE)

(*) Notice: Subject to any disclaimer, the term of this patent is extended or adjusted under 35 U.S.C. 154(b) by 504 days.

(21) Appl. No.: 14/360,018

(22) PCT Filed: Nov. 26, 2012

(86) PCT No.: PCT/GB2012/052917
§ 371 (c)(1),
(2) Date: May 22, 2014

(87) PCT Pub. No.: WO2013/076512
PCT Pub. Date: May 30, 2013

(65) Prior Publication Data
US 2015/0029813 A1 Jan. 29, 2015

(30) Foreign Application Priority Data
Nov. 25, 2011 (GB) .................................. 1120390.8

(51) Int. Cl.
G01N 21/25 (2006.01)
G01J 3/46 (2006.01)
(Continued)

(52) U.S. Cl.
CPC ........ G01J 3/463 (2013.01); B01F 15/00214 (2013.01); G01J 3/0205 (2013.01);
(Continued)

(58) Field of Classification Search
CPC . B01F 15/00214; G01J 3/463; G01N 21/8507
See application file for complete search history.

(56) References Cited

U.S. PATENT DOCUMENTS 2,253,551 A 8/1941 Booge
2,488,440 A 11/1949 Holger
(Continued)

FOREIGN PATENT DOCUMENTS

DE 2531459 2/1977
DE 4333138 3/1995
(Continued)

OTHER PUBLICATIONS

Gardner/Sward Paint—Testing Manual, 13th Ed, 1972, pp. 41-49.
(Continued)

Primary Examiner — Tony G Soohoo
Assistant Examiner — Elizabeth Insler
(74) Attorney, Agent, or Firm — Parsons Behle & Latimer

(57) ABSTRACT

A method is provided for testing a diffusely reflective liquid for color strength, said liquid comprising particles in a carrier medium, e.g. white emulsion paint based on titanium dioxide. The method comprises measuring in situ a lightness parameter of the liquid, of the carrier medium and of the liquid diluted with amounts of carrier medium; and determining from said measurements a dilution parameter indicating the amount of carrier medium needed to produce a predetermined reduction in the lightness parameter of the liquid, said dilution parameter providing an indication of color strength. The lightness parameter may be L* in the CIE L*, a*, b* color space, and the test may be carried out using a diffuse reflection probe (10) configured to direct light from said probe (10) into the liquid and configured to collect a portion of the light from the probe (10) diffusely reflected by the paint for determining the lightness parameter. The results may be used for process control e.g. in emulsion paint manufacture.

11 Claims, 3 Drawing Sheets

(51) Int. Cl.
    *B01F 15/00*     (2006.01)
    *G01N 21/47*     (2006.01)
    *G01J 3/02*     (2006.01)
    *G01J 3/50*     (2006.01)

(52) U.S. Cl.
    CPC ........... *G01J 3/0208* (2013.01); *G01J 3/0218* (2013.01); *G01J 3/465* (2013.01); *G01J 3/50* (2013.01); *G01N 21/251* (2013.01); *G01N 21/255* (2013.01); *G01N 21/474* (2013.01); *B01F 2215/005* (2013.01)

(56) References Cited

U.S. PATENT DOCUMENTS

| | | | |
|---|---|---|---|
| 3,208,866 A | | 9/1965 | Lewis |
| 3,286,992 A | | 11/1966 | Armeniades |
| 4,062,524 A | | 12/1977 | Brauner |
| 4,279,512 A | | 7/1981 | Tunstall |
| 4,511,251 A | | 4/1985 | Falcoff |
| 4,643,584 A | | 2/1987 | Allocca |
| 4,887,217 A | | 12/1989 | Sherman |
| 4,936,685 A | * | 6/1990 | Taylor ................. G01J 3/46 356/246 |
| 5,990,486 A | | 11/1999 | Chen |
| 6,040,913 A | * | 3/2000 | Johnson ............... G01N 21/532 106/436 |
| 6,118,520 A | | 9/2000 | Harner |
| 6,236,460 B1 | | 5/2001 | Johnson |
| 6,917,424 B2 | | 7/2005 | Rodrigues |
| 7,911,615 B2 | | 3/2011 | Martino |
| 2002/0149773 A1 | * | 10/2002 | Martino ................ G01N 21/05 356/436 |
| 2002/0167663 A1 | * | 11/2002 | Martino ................ G01N 21/27 356/319 |
| 2002/0174804 A1 | | 11/2002 | Rodrigues |
| 2004/0125691 A1 | | 7/2004 | Streiff et al. |
| 2005/0002027 A1 | | 1/2005 | Sierakovski |
| 2011/0075512 A1 | | 3/2011 | Pappalardo |

FOREIGN PATENT DOCUMENTS

| | | | |
|---|---|---|---|
| GB | 1589705 | 5/1981 | |
| GB | 2061746 | 5/1981 | |
| JP | 2000301698 | 10/2000 | |
| WO | WO 2007097996 A2 * | 8/2007 | ............ G01N 21/31 |

OTHER PUBLICATIONS

Chantrapornchai, Colloids and Surfaces A: Physicochemical and engineering aspects, 166 (2000) 123-131.
International Search Report issued in PCT/GB2012/052917 dated Jun. 6, 2013.
International Search Report issued in PCT/GB2012/052917 dated Mar. 4, 2013.
Search Report issued in GB1120390.8 dated Mar. 23, 2012.

* cited by examiner

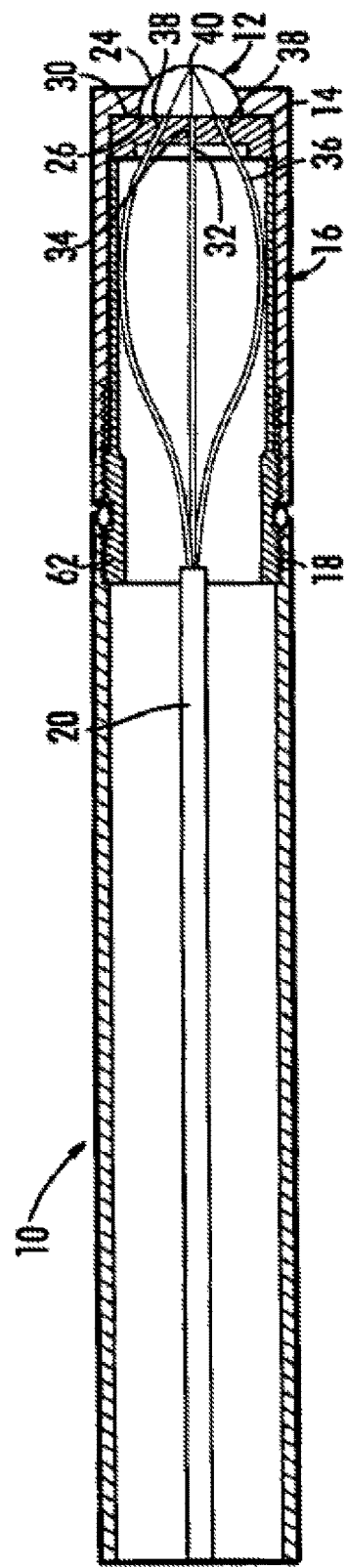
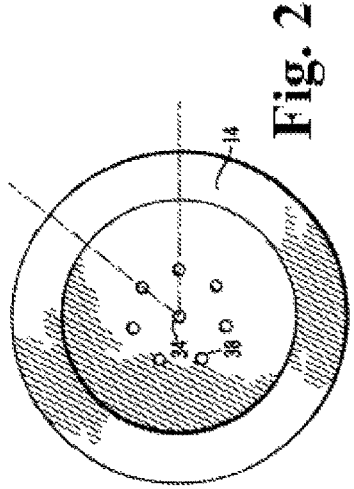
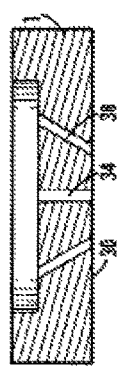
Fig. 1
Fig. 2
Fig. 3

COLOUR STRENGTH MEASUREMENT AND ITS USE IN PRODUCTION PROCESSES

CROSS-REFERENCE TO RELATED APPLICATIONS

This application is the National Stage of International Application No. PCT/GB2012/052917 filed Nov. 26, 2012 which claims priority under 35 U.S.C. § 119(b) from Great Britain Patent Application No. 1120390.8 filed Nov. 25, 2011 the entire contents are hereby incorporated by reference in their entirety.

FIELD OF THE INVENTION

This invention relates to a method for testing for colour strength of a diffusely reflective liquid e.g. paint, and to a method for controlling the colour strength of the liquid by using the measured colour strength to facilitate adjustment of the colour strength of the fluid and bring it to within an intended range of values.

BACKGROUND TO THE INVENTION

It is known to evaluate the so-called tinting strength of an individual pigment e.g. titanium dioxide or another white pigment. Such a method is disclosed e.g. in U.S. Pat. No. 2,253,551 (Booge) and involves providing standards by milling together a standard titanium dioxide pigment, refined linseed oil and varying amounts of ultramarine blue, the samples being graded by viewing the sample paste on a microscope slide. For a test pigment the colour strength is determined by the amount of the ultramarine blue to give a desired strength and such methods have become established in the art and survived for a long time, see e.g. U.S. Pat. No. 3,208,866 (Lewis) at column 6 lines 63-66.

It is known, however, that tinting strength of an individual pigment or of a group of pigments cannot be simply related to their performance in paint. This may be illustrated with reference to titanium dioxide which is the most important white pigment used in the coatings industry.

Titanium dioxide (TiO2) and other white pigments opacify paint films primarily by diffusely reflecting light. This reflection occurs because the white pigment scatters or bends light strongly. If there is enough white pigment in a paint film, almost all visible light striking it (except for a very small amount absorbed by vehicle or pigment) will be reflected, and the film will appear opaque, white, and bright. A change of refractive index promotes reflection and reflection of light will occur from the surface of $TiO_2$ pigments with high refractive index (2.7) in contact with various coatings vehicles at low refractive index (e.g. about 1.5). Part of the light is refracted within the particles, and the higher the refractive index the shorter the path of the light within the film and the less depth of film needed to give a white rather than a grey colour when viewed over a dark background. Furthermore when the size of the $TiO_2$ particles approaches half the wavelength of incident light, the particles can bend four to five times as much light as actually falls on them because a large amount of the light is diffracted when it passes close to the particles. In other words, the scattering cross section can be four to five times the geometric cross section of the particles. $TiO_2$ is unique in that it combines high refractive index with a high degree of transparency in the visible region of the spectrum (although diffraction is also affected by volume concentration of the pigment and by "dry flat hiding" if air becomes incorporated into the film). One way to incorporate air into the paint in a stable manner is by adding porous materials which only reach their final optical properties in the dry state after the solvent has evaporated. This combination of properties affords the coatings formulator a route to highly opaque and bright whites or tints at minimum film thicknesses. For most efficient light scattering, the $TiO_2$ pigment diameter should be slightly less than one-half the wavelength of light to be scattered. Since the human eye is most sensitive to yellow-green light (wavelength about 0.55 µm), the theoretical optimum particle size for $TiO_2$ pigments for coatings is between 0.2 and 0.3 µm in diameter.

In addition to $TiO_2$ and vehicle, many paints also contain extender pigments. These materials perform a variety of functions. White extender pigments are mineral compounds of relatively low refractive index and differ in composition, size and shape. They develop very little hiding in gloss and semi-gloss paints, but contribute dry-flat hiding (air-pigment interface) to paints at low cost and are used to control gloss, texture, suspension, and viscosity. The main types of extenders are carbonates, silicates, sulphates, and oxides. Their particle size ranges from 0.01 to 44 µm. High-gloss white paint usually contains only $TiO_2$; a semi-gloss paint contains $TiO_2$ and some extender pigments; a flat paint contains $TiO_2$ but has a high extender content.

The particle size of $TiO_2$ is small compared to the thickness of the film in which it is used. As discussed above. It has a theoretical optimum particle size between 0.2 and 0.3 µm, but as received by paint manufacturers is considerably larger because of the formation of agglomerates as a result of handling during the manufacturing process. The energy of simply stirring pigment into water or binder is not sufficient to overcome the particle attractive forces resisting the breakup of the agglomerates. By not minimizing the number of these agglomerates, the end-use properties will all be adversely affected. Although the pigment is designed to yield optimum hiding power, gloss and colour, these basic properties may not be realized if the initial dispersion of $TiO_2$ is inadequate. The optimum dispersion for the pigment is defined where further grinding will not change its particle size distribution. A further problem is flocculation i.e. formation of loose clumps of $TiO_2$ particles (i.e., flocculates) in a fluid system. Flocculation is often the result of an inadequate initial grind (dispersion), improper type or concentration of dispersant, pH mismatch, and temperature. Characteristically, these clumps are easily broken under moderate shear, but will quickly reform if the particles are free to move in the matrix. Flocculation can cause major problems, including loss of opacity and tinting strength.

Similar phenomena can occur with other pigments, whether white or coloured, and the colour strength and other properties of a pigment dispersion are not simply related to the nominal values of the pigment as supplied because it is essential to take into account agglomeration, flocculation and other phenomena to which the pigment may be subject.

US 2002/0174804 (Rodrigues) is concerned with making pigment dispersions that match a standard dispersion. It explains that it is important to carefully control these pigment dispersions with regard to tinting strength and colour through particle size adjustments as they are being made, so that when they are used in specified proportions to produce a desired paint, the load colour of the paint is easily shadeable/adjustable to an acceptable match to the standard colour for the paint. Acceptability of a grind was determined by traditional strength testing, which is a manual process that involves blending the dispersion with a standard white or black paint, spraying the blend onto panels, baking the panels and then comparing the panels to those of a standard batch of that dispersion blended with the same standard white or black using a spectrophotometer. Lightness differences between the dry sprayouts were then used as an indication of strength and acceptability of the grind. The improvement over traditional methods involved flowing the dispersion through a cell having a path length of e.g. 10-250 µm and viewing the dispersion in transmission at wavelengths from 400-700 nm. In embodiments the spectral transmission curve was measured and $L^*$, $a^*$ and $b^*$ or other suitable colour values for the standard liquid dispersion which the dispersion being produced is to match were determined. Once the pigment concentration and relative strength had been determined, the process could also include analysing the spectral transmittance of the resulting dispersion to determine colour acceptability for use in finished paints where the dispersion is the prime dispersion or a significant component thereof. Even when strength was equal to that of the standard, the dispersion could be calorimetrically unacceptable owing to batch-to-batch pigment variability. In order to monitor these colour changes and indicate whether the colour is acceptable for use the spectral transmittance of the resulting dispersion was measured by the spectrophotometer and the $L^*$, $a^*$ and $b^*$ colour values of the dispersion were then calculated from these measurements. A computer took these $L^*$, $a^*$ and $b^*$ values and determined their differences from the $L^*$, $a^*$ and $b^*$ values for the standard dispersion and from the magnitude of the numbers, determined the colour acceptability of the dispersion. However, the Rodrigues approach is only applicable to materials that can be viewed in transmission, and cannot be used for paint.

To the best of the applicants' knowledge and belief the Rodrigues technique has not found application in the paint industry. Currently the standard way of measuring colour strength or tinting strength of paint (as an example $TiO_2$ based white paint or any other coloured paint) is as follows. A sample of such paint is mixed with a known, well characterized tinting agent of known colour in a defined ratio. The diluted sample is used to form a coating on a substrate which is then dried in an oven and measured with a lab-based colour measurement instrument. The tinting strength is then given by the amount of dilution necessary to generate a particular response from the colour measurement instrument (e.g. a particular set of $L^*$, $a^*$, $b^*$ values, describing the coordinates of the colour in a 3-dimensional colour space). The process is time consuming (a single test can take about two hours), lab based, relies on a specific, well characterized tinting agent and does not lend itself to automation.

White emulsion paints are commonly based on inorganic pigments such as titanium dioxide and extenders e.g. calcium carbonate, kaolin, talc, silica and mica. These ingredients are mixed e.g. batch-wise 5000 liters at a time with vinyl emulsion and other materials in large tanks. Checking the colour strength by traditional methods takes up to two hours for a single measurement and significantly slows the production process, since the information is needed to determine whether or not additional ingredients or other processing measures are needed to bring the batch within its intended specification. The same is true when tinting agents are added to the paint. A problem that is addressed by the invention is the provision of a method for checking the colour strength of paint or other generally non light-transmissive e.g. diffusely reflective materials which is simple to carry out and takes a shorter time than the traditional method. A further problem is to provide a test method which lends itself to automation.

SUMMARY OF THE INVENTION

In one aspect the invention provides a method for testing a diffusely reflective liquid or an ink for colour strength, said liquid comprising particles in a carrier medium, which method comprises:

measuring in situ a lightness parameter of the liquid, of the carrier medium and of the liquid diluted with amounts of carrier medium or of the carrier medium diluted with varying amounts of the liquid; and determining from said measurements a dilution parameter indicating the amount of carrier medium needed to produce a predetermined reduction in the lightness parameter of the liquid, said dilution parameter providing an indication of colour strength.

Colour strength determined by the above method may be used in paint and pigment manufacture for adjustment of the paint or pigment using the measured colour strength to set that strength to within intended values. For example, measured colour strength may be used to determine the end point of a pigment grinding process. Measured colour strength may also be used to adjust pigment particle size, pigment particle size distribution and/or the narrowness or breadth of the particle size distribution in a paint or paint base material. It may be used to adjust the amount of mechanical dispersion imparted to pigment in paint or paint base dispersed in water or other dispersant, such dispersion e.g. being imparted by high speed dispersion blades or impellers which in addition to dispersing particles of pigment in water or other dispersion medium can also change the particle size distribution. Further measures may include e.g. adjustment of the proportion of pigment to diluent, adjustment of the proportion of titanium dioxide to calcium carbonate, talc, china clay or other extenders, adjusting amounts of wetting agent and other equivalent methods known to paint and pigment chemists.

In another aspect, the invention provides apparatus for mixing paint, comprising: a mixing tank; a sampler for removing a paint sample from the mixing tank; a test unit for testing diluent, samples of diluent mixed with progressively increasing amounts of the paint sample or paint sample mixed with progressively increasing amounts of diluent and the undiluted paint sample; an immersion probe configured to become immersed in liquid in the sampler; a spectrophotometer configured to supply light to the probe for illuminating the liquid and to collect and analyse light from the sample; a data analysis program configured to determine $L^*$ for the liquid under test, and from a series of measurements to determine a dilution parameter needed to bring about a predetermined reduction in $L^*$; and means for outputting the dilution parameter to a resource e.g. a display, a printer, a network or a process control unit.

In a further aspect there is provided apparatus for mixing liquids comprising first and second liquid flow lines, a static mixer connected to the first and second flow lines for receiving liquid from them, a measurement chamber for receiving liquid from the static mixer and an optical probe in the measurement chamber for measuring properties of the mixed liquid.

The above apparatus may further comprise a second static mixer connected to the measurement chamber at a side opposite to the first static mixer and third and fourth lines, the apparatus being configured for bidirectional flow and measurement. It may also comprise pumps e.g. metering pumps in the lines and it may be configured for measurement under continuous flow or stopped flow. The optical probe may be an immersion probe configured to collect light diffusely reflected from the liquid. A microcontroller or other device may be connected to valves and pumps of the apparatus for controlling operation thereof.

In a further aspect the invention provides a method of mixing first and second fluid streams which comprises passing the fluid streams into apparatus as defined above and using the probe for monitoring the results of mixing. The flow rate of the second stream may in some embodiments be 1-20 times the flow rate of the first stream, e.g. 5-15 times that of the first stream e.g. about 10 times that of the first stream.

Other preferred features will be apparent from the description below and from the accompanying claims to which attention is directed.

BRIEF DESCRIPTION OF THE DRAWINGS

How the invention may be put into effect will now be described, by way of example only, with reference to the accompanying drawings, in which:

FIG. 1 is a view in longitudinal section of a diffuse reflection probe which may be used in the method of the invention;

FIG. 2 is a view of a guide ring forming part of the probe of FIG. 1 showing a rearward face of the guide ring; and FIG. 3 is a section of the guide ring of FIG. 2 on the two lines appearing in that figure;

DETAILED DESCRIPTION OF PREFERRED EMBODIMENTS

Figure 4:
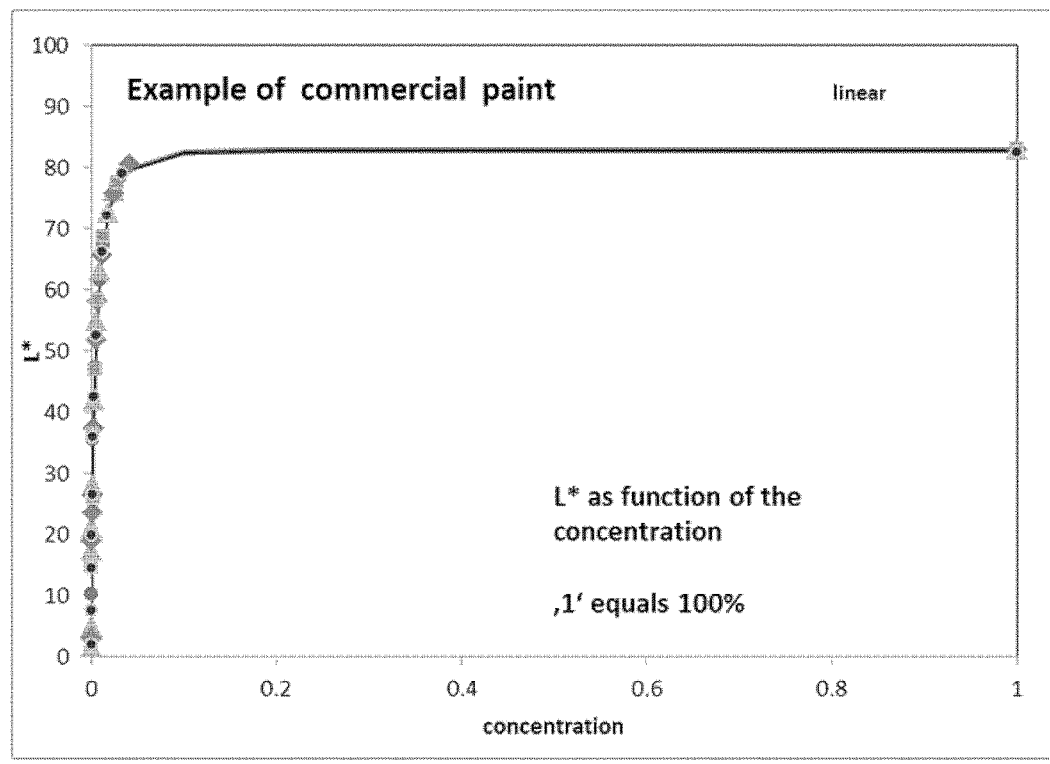
FIGS. 4 and 5 are curves showing measured L* as a function of concentration for carrier medium, diluted and undiluted white emulsion paint with concentration being shown on linear and logarithmic scales.

In the above mentioned method the diffusely reflective liquid may be paint, in some embodiments emulsion paint and in particular embodiments white emulsion paint or other white paint. The measurement may be carried out using polychromatic light or white light e.g. from a xenon flash lamp. The measured lightness parameter may be L* in the CIE L*, a*, b* colour space, and the predetermined reduction may be 1/e, ½ or other equivalent reduction. The lightness parameter may be measured using light diffusely reflected from the liquid, e.g. by a diffuse reflection probe configured to direct light from said probe into the liquid and configured to collect a portion of the light from the probe diffusely reflected by the paint for determining the lightness parameter. Thus there may be employed a probe for contact with the test liquid, which comprises:

a lens having a flat rear face and a generally hemispherical front face that provides a surface for contacting said test liquid and that resists adherence of solids to said lens;

a plurality of transmitting fibres each angled relative to the rear face of the lens so that in use light emerging from said transmission fibres converges at or adjacent a foremost part of said lens; and a light-receiving fibre directed generally normal to the rear face of the lens for receiving a portion of the transmitted light gathered by the lens from the test liquid.

The test liquid may be moving relative to said probe, e.g. the test liquid may be stirred or pumped past the probe.

In the above mentioned apparatus the immersion probe may be configured to collect light diffusely reflected from the liquid and means may be provided for maintaining relative movement between the test liquid and the probe, e.g. a stirrer or a pump.

An embodiment of the present method is laboratory based, uses simple apparatus, and can carry out a single measurement in about 25 minutes (possibly as little as 10-15 minutes) rather than the two hours needed for the traditional method. Sample material e.g. sampled paint in the course of mixing is added progressively to liquid medium and L* is measured as a function of concentration in the medium. Typically about 5-15 measurements are made for a single sample, and it is desirable to use a logarithmic scale with several decades of concentrations. A single measurement can take 30-90 sec, the determining factor being the time needed to achieve a homogeneous mixture on which the measurement can be taken. It has been found that the data obeys an analytical function which is advantageous because curve-fitting can be employed. A dilution parameter is estimated from the function, being a dilution parameter V[L*(c=(100%/V)=½ L*(c=100%)], i.e. how much must the test material be diluted so that L* falls to half? For a range of currently commercially available white emulsion paints which have L*, a*, b* values in a narrow range, it has been found that V falls in the range 25-400 as indicated below which is a surprisingly wide range of variance. The measurement is in terms of colour strength and is self-calibrating, with the entire range of values of L* (c) for values of c from 0.1% to 100% being determined. As described below, the data points are fitted to a sigmoidal curve with parameters p, q, r and s, the parameters r and s describing the fall of the curve with decreasing concentration. The method enables relative process parameters to be obtained, especially for $TiO_2$-based materials. The multiplicity of measurements taken enables statistical analysis to be applied and error bars to be generated. Automation may reduce the measurement time from the values indicated above.

It is believed that the present procedure can be developed to provide an automated sequence of measurements at or adjacent to an industrial mixing tank e.g. for final mixing of paint in batches of some thousands of liters each e.g. 1000 liters-10,000 liters e.g. about 5000 liters. Furthermore, measurements taken during addition of pigment to give as little as 10% of the final concentration may enable accurate predictions of the expected colour strength and to provide directions for addition of the remaining approximately 90%.

The present method can be developed and brought into use in phases. It can be laboratory verified for a new installation, used as a stand-alone method or used for inline measurements on the mixer.

Consideration has been given to possible sources of error in the proposed method. In the present method the greatest sources of error have been found to be the variations in concentration of each sample, but the variability in a series of measurements is significantly less than the scatter from measurement to measurement, so that the use of a series of measurements as in the present method helps to achieve the necessary accuracy.

An embodiment of the method works by directing polychromatic and in a more specific embodiment white light as from a xenon flash lamp into dispersion medium or samples made by mixing the dispersion medium with progressively increasing proportions of test liquid e.g. paint including undiluted test liquid e.g. paint, allowing the light to become scattered by particles in the paint or other test liquid, collecting some of the scattered and diffusely reflected light and using that light to measure the optical properties of the paint or other test liquid, and in embodiments its L* value. The light may be from a xenon flash lamp and may be continuous spectrum light in the visible range e.g. white light of 300-700 nm wavelength. Coordinates L*, a* and b* refer to the CIE 1976 colour space, the lightness correlate L* being calculated using the cube root of the relative luminance and closely matching the human perception of lightness. Values of L* range from black (0) to diffuse white (100).

In some embodiments, it is convenient to start with the dispersion medium, taking successive measurements with progressively increasing proportions of neat paint or other test fluid and ending with the undiluted paint or test fluid. Thus it is convenient to start, in the case of paint, with measuring the properties (e.g. L*, a*, b*) of a clear carrier medium, proceed by measuring several (L*, a*, b*) values of (carrier medium+various, defined amounts of paint) and finishing by measuring the (L*, a*, b*) of the undiluted paint. In other embodiments, is convenient to start with the neat paint or other test fluid, taking successive measurements with progressively increasing proportions of dispersion medium and ending with dispersion medium containing only a trace of paint. Thus it is convenient to start, in the case of paint, with measuring the properties (e.g. L*, a*, b*) of undiluted paint, proceed by measuring several (L*, a*, b*) values of (carrier medium+various, defined amounts of paint) and finishing by measuring the (L*, a*, b*) of the highly dilute paint. Measurement can be of the colour strengths directly in the liquid paint without using a tinting agent (tinter-less). There can be used uses a colour measurement instrument developed for in-situ measurement of properties of liquid media, including a dedicated liquid colour measurement probe.

We then take the acquired data, in particular the L*(c), c being the concentration of paint in the carrier medium and fit a specific analytical function to the data from which we extract the functional parameters. This allows us to determine a 'dilution parameter' with very high accuracy because we use all data points for a regression analysis. This 'dilution parameter' characterizes the amount of carrier medium necessary to reduce the L* of the undiluted paint for example to ½ or 1/e. This parameter corresponds to the traditionally measured colour strength values and a onetime calibration with the lab based technique allows the direct correlation of both the traditional and our new approach.

We can use an immersion probe for measuring the optical characteristics of reflective pigmented liquids by contact directly in the wet, e.g. the characteristics of emulsion paint. It may be a diffuse reflection probe as shown in the drawings. The disclosed embodiment of such a probe (which is only an example of the kind of device that might be used) directs light at various angles into the paint or other liquid and detects diffusely reflected light from the liquid so as to facilitate measurement of the optical properties e.g. the L*a*b* of the test liquid e.g. using a spectrometer.

Referring now to the drawings, the probe, generally indicated by reference number 10 has five main components. It has a lens 12 e.g. of sapphire, a guide ring 14, an anterior housing 16, a sleeve 18, and optic fibre bundle 20. Sapphire is a suitable lens material inter alia because off its high refractive index, being 1.78 whereas that of fused silica is 1.46, that of crown glass is typically 1.62 and that of flint glass is 1.58**. Lens 12 is a hemispherical lens and has a spherical front face 24 and a flat rear face 26, the lens being transparent to the measurement light and the focal point being close to the lens. Guide ring 12 fits behind lens 12 (when the spherical front face 24 of lens 12 is considered to be forward) and has front face 30. The ring 14 has one central hole 34 dimensioned to receive a single optic fibre 32 (reflection optical fibre) and one or more surrounding holes (in an embodiment seven) 38 evenly spaced around the central hole, each of which is also dimensioned to receive a single optic fibre 36 (transmission optical fibres). Central hole 34 is formed to be perpendicular to a front face 30 of guide ring 14 and the surrounding holes 38 are formed to be at an angle with respect to front face 30, preferably 29° with respect to front face 30. The 29° angle is desirable because, when the fibres are fixed into the guide ring and polished flat, the light exits the probe at 45° in air (the angle may be set differently for emergence into emulsion paint). The thickness of guide ring 14 and the radial positions of surrounding holes 38 are selected so that, when front face 30 of guide ring 14 is placed against the rear face 26 of lens 12, light beams emerging from fibres 38 converge at the foremost part 40 of spherical front face 24 of lens 12 in line with central hole 34. Directions for the fibres may alternatively be considered with reference to the plane of the rear face of the lens and directions which are orthogonal to that plane or inclined with reference to that plane.

It is desirable, though not essential in all embodiments, that lens 12 be hemispherical. Such a lens provides a good shape for the optical requirements of the probe system and is not difficult to make. The curve of a hemispherical lens can fit snugly against the hemispherical contour of the forward end of anterior housing 16 for a good fit. Other combinations of corresponding shapes will provide a good seal notwithstanding the fact that they may be more difficult and expensive to make. A hemispherical lens provides an optically convenient surface for the convergence of light from surrounding optic fibres 36 and has been found in practice to be resistant to unwanted deposition of pigment particles. In particular, when conducting measurements on paint, it has been found that a relatively small degree of relative movement between the paint or other test liquid and the lens as by stirring the paint or other test liquid or pumping the paint or other test liquid past the lens is sufficient to avoid or largely avoid deposition of aggregates of pigment particles on the lens.

In use, the probe is immersed in the liquid to be measured and light is directed through the seven surrounding optic fibres 36 into the paint or other test liquid. The light from surrounding optic fibres 36 converges on foremost point 40 of lens 12 and is diffusely reflected by the paint or other test liquid. A portion of the diffusely reflected light is picked up by central optic fibre 32 and returned to a spectrometer for analysis of the L*A*B* values based on its reflection spectrum.

Figure 5:
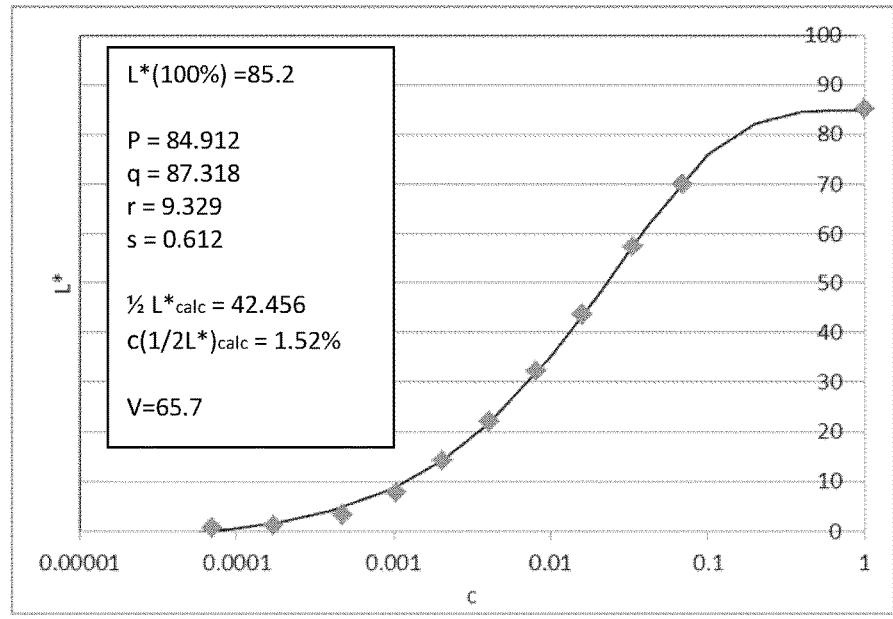

In order to demonstrate the above method, tests were carried out on a sample of commercially available emulsion paint. Initially 1 liter of diluent for the paint was added to a small beaker equipped with a stirrer. A CP colour probe (ColVisTec) as described above was immersed into the diluent, light from a xenon flash lamp forming part of an inline colour spectrophotometer was passed down the probe and into the liquid and collected light was returned to the spectrophotometer and analysed using EquiColor™ (Equitech International) which is a software package allowing L*, a* and b* values to be calculated. In a series of measurements, paint was added progressively to the diluent and the spectra at each dilution were measured, and finally the same measurement was made on the undiluted paint, giving data sets of which a representative one is set out below. If L* is plotted against proportion of paint, a rising curve is obtained as in FIG. 4 which is difficult to measure. On a logarithmic scale as in FIG. 5 a sigmoidal curve is obtained for which best fit parameters can be derived using curve fitting. For the indicated data set the mathematical expression used was:

$$Y(x) = p - qe^{r e^{x^s}}$$

where ^ indicates that the power term for e can more clearly be written $-qx^s$. For the data set below, values of these parameters as calculated by the software (with spurious over-precision) is p=84.912, q=87.318, r=9.329 and s=0.612. From the fitted curve it is possible to calculate a value p, q, r and s and a dilution parameter V=65.7

| Add. No. | Paint added (grams) | Total (grams) | L"A" (measured) | L"A" (calc) | Δ2 |
|---|---|---|---|---|---|
| 0 | gramm | 1.00E−05 | 9.979E−09 | −2.39612265 | |
| 1 | 0.025 | 0.02501 | 2.4957E−05 | 0 | −1.1704471 | 1.36994642 |
| 2 | 0.046 | 0.07101 | 7.0856E−05 | 0.58 | −0.08096243 | 0.43687134 |
| 3 | 0.102 | 0.17301 | 0.00017262 | 1.27 | 1.56429957 | 0.08661224 |
| 4 | 0.302 | 0.47501 | 0.00047379 | 3.38 | 4.81445492 | 2.05766091 |
| 5 | 0.576 | 1.05101 | 0.00104771 | 7.75 | 9.02092082 | 1.61523974 |
| 6 | 1.012 | 2.06301 | 0.00205446 | 14.24 | 14.2579327 | 0.00032158 |
| 7 | 2.034 | 4.09701 | 0.00407178 | 22.15 | 21.6206304 | 0.28023215 |
| 8 | 4.068 | 8.16501 | 0.00808205 | 32.18 | 31.3913757 | 0.62192835 |
| 9 | 8 | 16.16501 | 0.01587505 | 43.69 | 43.2427191 | 0.20006025 |
| 10 | 18.324 | 34.48901 | 0.03327163 | 57.5 | 57.6302546 | 0.01696627 |
| 11 | 39.6 | 74.08901 | 0.06884386 | 69.95 | 70.6944571 | 0.55421633 |
| 12 | | undiluted | 1 | 85.2 | 84.9042046 | 0.08749495 |

A number of tests were carried out with different paints and dilution factors were measured as in the table below, from which an indication may be gained of the variability in dilution factors measurable for apparently similar white paint. It was found that the pattern of variation in these dilution factors closely reproduced the pattern obtained using traditional tests as set out below:

| | Dilution factor | L* (c = 100%) | a* | b* |
|---|---|---|---|---|
| Emulsion 1 interior white | 65.68 | 85.20 | 0.07 | 0.95 |
| Emulsion 2 interior room | 66.31 | 85.87 | 0.00 | 1.15 |
| Emulsion 3 interior silk | 353.08 | 84.55 | −0.28 | −0.75 |
| Emulsion 4 interior easy | 102.12 | 85.73 | −0.43 | 0.71 |
| Emulsion 5 interior snow white | 190.77 | 83.69 | −0.14 | −0.10 |
| Emulsion 6 interior matt | 100.04 | 84.11 | −0.15 | −0.73 |
| Emulsion 7 interior premium matt | 67.27 | 83.60 | −0.10 | 1.05 |
| Emulsion 8 interior pl white | 25.72 | 84.66 | 0.02 | 0.25 |
| Emulsion 9 exterior pl white | 78.62 | 83.68 | −0.17 | 0.39 |
| Emulsion 10 interior pt matt | 146.29 | 81.50 | 0.18 | 2.25 |

The above method does not rely on a tinting agent, is rapid, and it is fast and can lead directly to in-line, in-situ measurements of colour parameters in a manufacturing setup. The method relates to a process for monitoring the progress of a reaction or a manufacturing process by using the diffuse reflection probe system disclosed herein.

In a further embodiment the process may comprise dilution is in a static mixer, and in a yet further embodiment undiluted liquid or liquid diluted with carrier medium is fed from the static mixer to an optical measurement chamber provided with a diffuse reflection probe configured to direct light from said probe into liquid in said chamber. The above apparatus may further comprise a static mixer for mixing the paint sample and diluent, and the static mixer may lead to an optical measurement chamber provided with the immersion probe. The static mixer may comprise a housing provided with a series of baffles e.g blades or "bow-tie elements" configured to mix incoming streams by flow division, radial mixing or equivalent processes.

Figure 6:
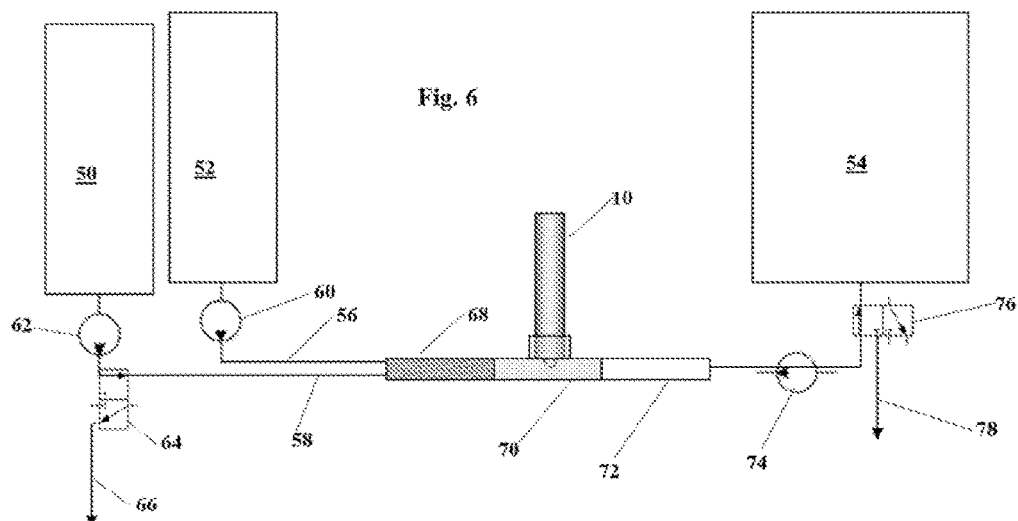
FIG. 6 is a schematic implementation of dilution apparatus for successive dilution of paint samples starting at concentrated paint with mixing by means of a static mixer.

A further embodiment of the invention is illustrated in FIG. 6 which shows apparatus for successive dilution of paint samples starting with concentrated paint. Paint reservoir 50 and solvent 52 are passed by high accuracy metering pumps 60, 62 and lines 56, 58 in a predetermined constant volumetric or mass ratio through in line static mixer 68. Such mixers have no moving parts, are powered by pressure difference and operate by radial transport of fluid streams passing through them and by dividing the fluid streams into multiple partial streams which are then recombined, and they may be based on baffles e.g. of grid type (e.g. X-grid crossing bar), corrugated plate type, helical or butterfly type or square geometry type in which a series of alternating left and right hand elements with intermittent flow inverters channels the fluids from the walls into the centre of the mixer and from the centre to the walls. They may be provided with pipe threads or other connector formations at each end to simplify in-line connection. The mixture of paint and diluent passes through optical measurement chamber 70 provided with probe 10 of the kind discussed above and thence via chamber 72 and pump 74 to a third reservoir 54 of sufficient volume to contain the mixture. Chamber 72 is provided to "balance" the mixer 68 so that there is no immediate discontinuity in the flow conditions of the sample as it leaves the measurement chamber 70.

For example, in-line static mixers which may be used in the above apparatus may be based on a tubular casing having two or more grids of elements arranged at angles to the longitudinal axis of the casing and to each other so that each intersects the other, the grids optionally being configured in relatively short axial sections each defining a mixing stage and differing from adjacent sections e.g. in rotational position of the mixing elements and/or in configuration of the mixing elements, see U.S. Pat. No. 3,286,992 (Armeniades), U.S. Pat. No. 4,062,524 (Brauner), U.S. Pat. No. 4,643,584, (Allocca), GB-A-2061746 (Streiff, Sulzer), US 2004/0125691 (Streiff et al.) and US 2011/075512 (Pappalardo, Nordson) the disclosures of which are incorporated herein by reference. Examples of such mixers are Sulzer type SMX and SMX plus in-line mixers that are designed to operate in laminar flow and SMV that are designed to operate in a turbulent flow regime. Similar mixers are made by other suppliers e.g. Stamixco (www.stamixco-usa.com) and Nordson (www.nordson.com). The latter company manufactures a range of mixers, including spiral mixers, in plastics materials e.g. acetal, polypropylene, nylon and fluoropolymer which may incorporate mixing elements injection moulded in one piece of "apple core" cross-section in e.g. polypropylene or fluoropolymer. It is believed that in context of paint and pigments, attack by the test material and diluent on mixing elements of moulded plastics may be relatively slow, and may predominantly be by abrasion so that replacement need not be after each element but may be periodic e.g. daily or weekly. The mixing element may be in a metal e.g. stainless steel sleeve. Threaded ends may be provided and in the case of an in-line plastics mixer the ends may fit into threaded metal pipe adaptors or connectors.

Data acquisition may be under moving flow of material, the pumps 60, 62 being in operation, or may be under stopped flow. In the case of pigment suspensions e.g. paint or paint base containing $TiO_2$ pigment, moving flow may be employed to avoid pigment particles settling on the immersed hemispherical lens of the probe. Flow is discontinued when sufficient data has been acquired to give a sufficiently accurate measurement flow from reservoirs 50 and 52 is discontinued. Valve 76 is operated to isolate the "first pass" material in reservoir 54, after which reservoir 50 is flushed with solvent which is exhausted via pump 62, valve 64 and exhaust line 66. Solvent from reservoir 52 via pump 60 flushes line 56, in-line mixer 68, chambers 70, 72 and then passes to exhaust line 78. Other lines may be flushed as needed. First pass material is then pumped from reservoir 54 by a line and pump (not shown) to reservoir 50, after which reservoir 54 is flushed with solvent which is discharged at line 78. The apparatus has now returned to the first stage and the "first pass" material is further diluted to "second pass" material which is optically measured in chamber 70 and passes to third chamber 54. Successive dilutions may be carried out in this way and depending on the ratio of solvent to paint at each pass in 5-10 passes the paint will become diluted to $10^{-4}$ to $10^{-6}$ of its original strength which will provide data along substantially the entire dilution curve. It will be appreciated that the method described above can be used to analyse relatively small samples initially present in reservoir 1 and that the process readily lends itself to automation. The static mixer 68 can be of relatively small volume so that there can be economy in sample size and volume of solvent used.

Figure 7:
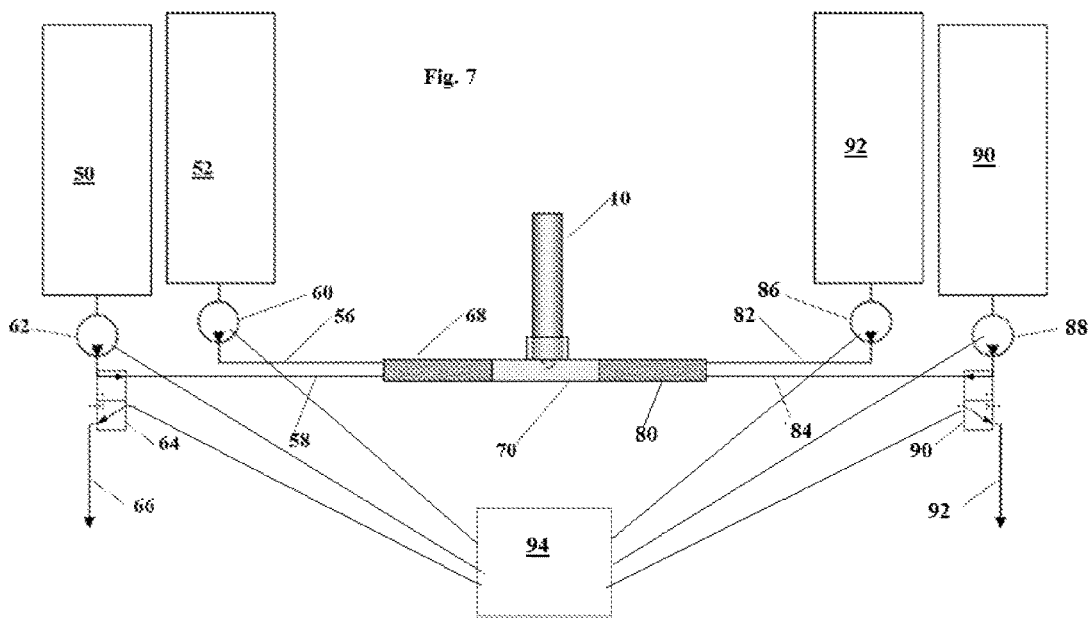
FIG. 7 is a schematic representation of a second dilution apparatus like that in FIG. 6 but configured for bidirectional operation, and also showing a associated microcontroller.

In FIG. 7, the apparatus is similar to that of FIG. 6 but is configured for bidirectional operation. Chamber 72 is replaced by a second static mixer 80 like the static mixer 68. Lines 82, 84 lead via metering pumps 86, 88 to sample chamber 90 and diluent chamber 92. Valve 90 in line 84 also leads to waste line 92 for discharge of the contents of sample chamber 90. Operation is generally as described above except that after the purge operation the contents of sample chamber 90 can be diluted with solvent from solvent chamber 92 in reverse flow and the "second pass" diluted mixture which flows through measurement chamber 70 can provide data as before, either in moving flow or in stopped flow depending on the material being tested. The diluted sample passes via first static mixer 68 and line 58 to chamber 50 which will have been purged. Purging and flow reversal then enables a "third pass" measurement to be made, and operations can be continued with reversed flow between each pass until a sufficiently dilute sample is obtained and data collection can be terminated. It will be appreciated that this embodiment, as also the FIG. 6 embodiment, lends itself to automation. For that purpose, by way of diagrammatic illustration, a control unit 94 is shown which may incorporate a microcontroller or equivalent device, electrical control lines being shown leading to pumps 60, 62, 86, 99 and valves 64 and 90. It will be appreciated that additional pumps, valves and lines may be added as necessary for adding a new test sample to chamber 50, adding diluent to chambers 52, 92 from reservoir tanks and for facilitating purge operations.

It will be appreciated that the foregoing description is by way of example only and various modifications may be made to the embodiments described above without departing from the invention. For example the in-line mixer embodiments have been described with reference to dilution of paint, but they are equally applicable to variants in which paint is progressively added to solvent and they are believed generally suitable for testing of addition of small amounts of material e.g. water-soluble colourants or suspended pigments to larger streams. In the embodiments shown the in-line mixers are shown as having axial lengths greater than their diameters, but disc-type mixers in which the axial length is less than the diameter could also be suitable in some embodiments e.g. mixers of the general proportions the Sulzer CompaX static mixers where axial length is only about 0.3 diameters. In these embodiments reduction of the axial length of the sample chamber to equal to or less than its diameter may also be possible. Cylindrical mixers are illustrated but other mixer profiles e.g. square mixers may also be employed.

The invention claimed is:
1. A method for testing a paint for a color strength, the method comprising:
providing a paint that is diffusely reflective and comprises particles in a dispersion medium, the particles being of titanium dioxide or other white pigment(s) which opacify the paint by diffusely reflecting light;
providing samples of a diluent, samples of the diluent each mixed with progressively increasing amounts of the paint or samples of the paint each mixed with progressively increasing amounts of the diluent, and of the paint;
immersing in each of the provided samples a probe configured to direct light from the probe into the samples and configured to collect a portion of the light from the probe diffusely reflected by the samples;
configuring a spectrophotometer to supply light to the probe for illuminating the samples and to collect and analyze light collected by the probe from the provided samples;
analyzing the light diffusely reflected from the samples using a software package and calculating a lightness parameter $L^*$ in the CIE $L^*$, $a^*$, $b^*$ color space for each of the diluent, the provided samples of the diluent mixed with progressively increasing amounts of the paint or of the paint mixed with progressively increasing amounts of the diluent, and of the paint; and
determining from the calculated lightness parameters for the samples a dilution parameter indicating the amount of diluent needed to produce a predetermined reduction in the lightness parameter of the paint, the dilution parameter providing an indication of color strength, the dilution parameter being derived by the software package by fitting data points for a logarithm of concentration c (where c can range from 0 for diluent to 1 for paint) and measured L*(c) to a sigmoidal curve and calculating the dilution parameter from the fitted sigmoidal curve.

2. The method of claim 1, wherein the predetermined reduction is 1/e.

3. The method of claim 1, wherein the predetermined reduction is ½.

4. The method of claim 1, wherein the particles comprise titanium dioxide.

5. The method of claim 4, wherein the particles further comprise an extender pigment.

6. The method of claim 1, wherein the paint is an emulsion paint.

7. The method of claim 1, wherein mixing is in a static mixer.

8. The method of claim 7, wherein paint or paint mixed with diluent is fed from the static mixer to an optical measurement chamber provided with a diffuse reflection probe configured to direct light from the diffuse reflection probe into paint in the chamber.

9. The method of claim 1, wherein the light diffusely reflected by the samples is collected using a diffuse reflection probe which comprises:
- a lens having a flat rear face and a generally hemispherical front face that provides a surface for contact with and immersion in the sample and that resists adherence of solids to the lens;
- a plurality of transmitting fibres each angled relative to the rear face of the lens so that in use light emerging from the transmission fibres converges at or adjacent a foremost part of the lens; and
- a light-receiving fibre directed generally normal to the rear face of the lens for receiving a portion of the light gathered by the lens from the sample.

10. The method of claim 9, wherein the sample is stirred or is pumped past the diffuse reflection probe.

11. The method of claim 1, further comprising outputting the dilution parameter to a resource, wherein the resource is a display, a printer, a network, or a process control unit.

* * * * *